United States Patent [19]

Taniguchi et al.

[11] Patent Number: 4,566,463

[45] Date of Patent: Jan. 28, 1986

[54] APPARATUS FOR AUTOMATICALLY MEASURING BLOOD PRESSURE

[75] Inventors: Satoru Taniguchi, Seto; Hideo Nishibayashi, Kakamigahara; Masahiro Uemura, Komaki, all of Japan

[73] Assignee: Nippon Colin Co., Ltd., Aichi, Japan

[21] Appl. No.: 601,222

[22] Filed: Apr. 17, 1984

[30] Foreign Application Priority Data

Apr. 25, 1983 [JP] Japan .................................. 58-072678

[51] Int. Cl.⁴ .............................................. A61B 5/02
[52] U.S. Cl. .................................... 128/682; 128/687; 128/666; 128/693; 128/694; 128/700
[58] Field of Search ................ 128/672, 677, 680–683, 128/687, 689–691, 693–694, 700, 664–667

[56] References Cited

U.S. PATENT DOCUMENTS

| | | | |
|---|---|---|---|
| 3,051,165 | 8/1962 | Kompelien | 128/667 |
| 3,149,628 | 9/1964 | Bolie | 128/680 |
| 3,156,237 | 11/1964 | Edmark, Jr. | 128/687 X |
| 3,742,938 | 7/1973 | Stern | 128/687 |
| 3,996,928 | 12/1976 | Marx | 128/683 X |
| 4,013,067 | 3/1977 | Kresse et al. | 128/666 |
| 4,050,452 | 9/1977 | Lee | 128/683 |
| 4,425,922 | 1/1984 | Conti et al. | 128/691 |

OTHER PUBLICATIONS

Patel et al., "Automatic Plethysmography"; *Med. and Biol. Engr.*, 7-1979, pp. 460-464.

*Primary Examiner*—Lee S. Cohen
*Assistant Examiner*—Angela D. Sykes
*Attorney, Agent, or Firm*—Parkhurst & Oliff

[57] ABSTRACT

An automatic blood pressure measuring apparatus including an occluding device having a cuff to apply a pressure to a body member of a subject, and a blood-pressure determining device to determine a blood pressure according to a variation in a pulse wave in relation to a change in the cuff pressure. The apparatus comprises a detector for monitoring a blood circulatory system of the subject, and generating signals representing an abnormality associated with the circulatory system. The apparatus further comprises a control device for actuating the occluding device to apply the cuff pressure to the body member, and causing the blood-pressure determining device to execute a predetermined series of blood-pressure measuring steps to measure the blood pressure, thereby permitting an automatic measurement of the blood pressure of the subject when the blood circulatory system is found abnormal by the detector.

12 Claims, 10 Drawing Figures

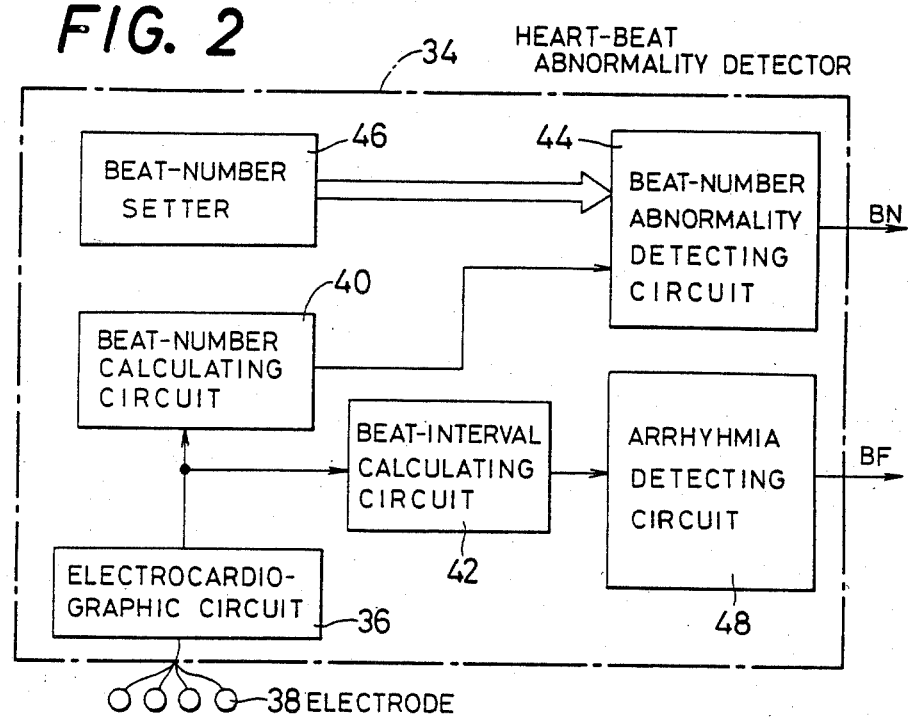
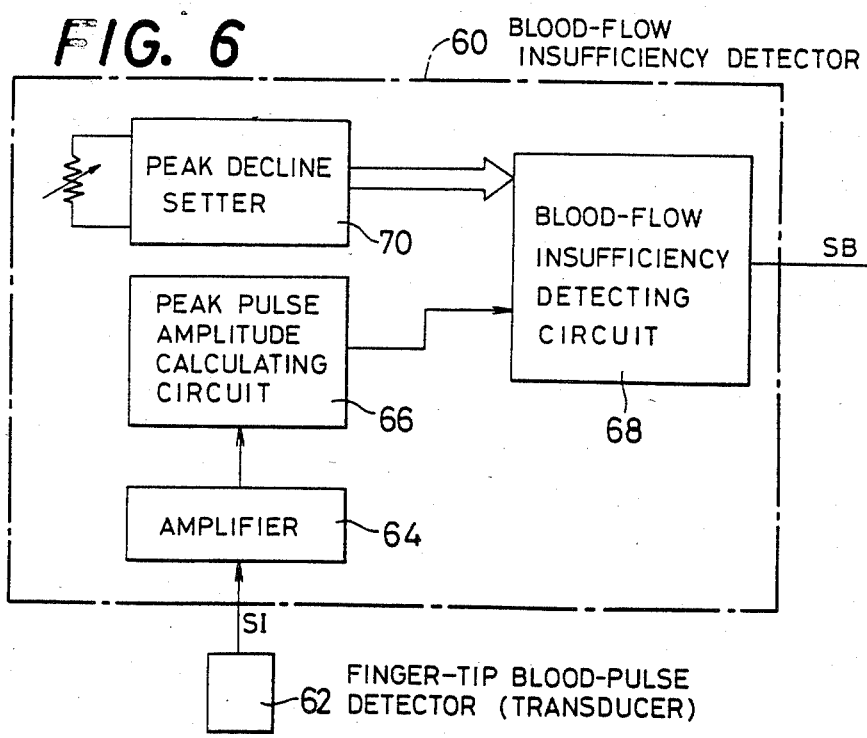

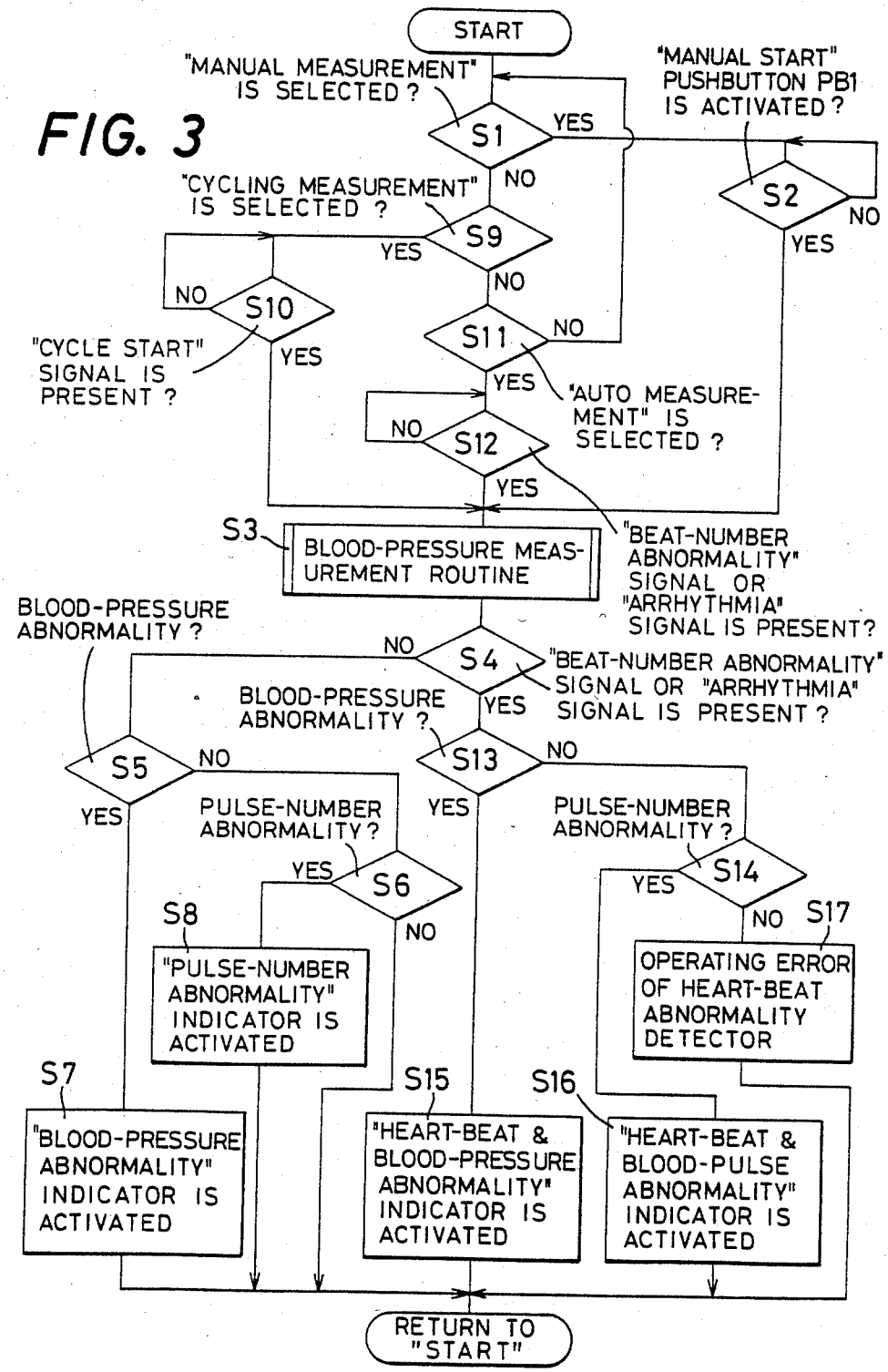

APPARATUS FOR AUTOMATICALLY MEASURING BLOOD PRESSURE

BACKGROUND OF THE INVENTION

1. Field of the Art

The present invention relates to an automatic blood-pressure measuring apparatus capable of automatically measuring blood pressure of a living subject such as a human body.

2. Description of the Prior Art

An automatic blood-pressure measuring apparatus is known, which comprises a cuff or occluding device for applying a pressure force to a body member of a living subject such as an arm or foot of a human or animal body, and blood-pressure determining means for determining blood pressure levels according to a variation in a blood pulse wave generated in relation to a change in the pressure force applied by the cuff device, for example, according to: presence or absence of Korotkoff sounds (blood sound waves) which are detected as sounds due to a blood flow through an arterial vessel of the subject; a variation in amplitude of cuff pressure pulsations generated in synchronism with beats of a heart of the subject; a variation in magnitude of pulsating movements of a wall of an arterial vessel of the subject which are detected by means of an ultrasonic wave. In the case where such an automatic blood-pressure measuring apparatus is used to monitor the subject (patient) for a comparatively long period of time in a continuous manner during or after a surgical operation of the subject, it is a common practice to repeat a blood-pressure measurement cycle periodically in response to an actuation signal which is generated at a predetermined time interval to actuate the measuring apparatus to execute a series of blood-pressure measuring steps.

In such a known type of automatic blood-pressure measuring apparatus wherein the blood pressure of the subject is measured periodically, there is recognized an inconvenience that a blood pressure measurement cycle does not always take place while there exists an abnormality or disorder associated with a blood circulatory system (circulatory organs) of the patient, for example: abnormal decrease in blood flow volume (blood insufficiency) at a certain point of the system, abnormal or irregular interval of heart beats, and abnormal number of the heart beats per unit time. In other words, the known arrangement fails to achieve the measurement at medically suitable timings at which the conditions of the subject can be well grasped. Stated the other way, to exactly grasp the conditions of the subject during or after a surgical operation thereof, it is medically preferred to know the blood pressure levels of the subject or patient during a time period while the subject is suffering from some functional trouble with the blood circulatory system.

In the meantime, it has been considered or proposed to shorten a time interval at which the actuation signals indicated above are generated, in order to activate the measuring apparatus more frequently, so that some of the measurement cycles are effected at timings closer to the period of abnormality in the blood circulatory system of the subject. In this instance, however, the body member is accordingly frequently occluded by the cuff, and the consequent frequent application of a cuff pressure to the body member will discomfort the patient.

SUMMARY OF THE INVENTION

The present invention was developed in view of the above described situation in the art. It is accordingly an object of the invention to provide an apparatus for automatically measuring blood pressure of a living subject when a functional abnormality of the blood circulatory system of the subject takes place.

According to the invention, there is provided an apparatus for automatically measuring blood pressure of a living subject, including an occluding device having a cuff for applying a pressure force to a body member of the subject, and blood-pressure determining means for determining the blood pressure according to a variation in a pulse wave generated at the body member in relation to a change in the pressure force applied thereto by the occluding device. The automatic measuring apparatus comprises:

(1) abnormality detecting means for monitoring a blood circulatory system of the subject for normal functioning thereof, and generating an abnormality signal representing an abnormality associated with the blood circulatory system; and (2) control means, responsive to the abnormality signal, for actuating the occluding device to apply the pressure force to the body member, and causing the blood-pressure determining means to execute a predetermined series of blood-pressure measuring steps to measure the blood pressure, thereby permitting an automatic measurement of the blood pressure of the subject when the blood circulatory system is found abnormal by the abnormality detecting means.

Advantages of the Invention

In the measuring apparatus constructed as described above, an abnormality signal is generated from the abnormality detecting means upon detection of abnormalities associated with the blood circulatory system, such as an abnormal decrease in blood flow volume through arteries in an outer extremity or peripheral portion of the subject, an abnormal interval of heart beats of the subject, or an abnormal number of the heart beats per unit time. In response to each abnormality signal, the control means directs the apparatus to initiate a predetermined series of blood-pressure measuring steps to measure the blood pressure upon generation of the abnormality signal. Thus, the measurement of the blood pressure is made at the time of occurrence of such abnormal condition of the circulatory system, which is a medically or diagnostically important blood-pressure measuring timing for recognizing the condition of the subject during or after a surgical operation thereof. This arrangement does not conduct measurement cycles unnecessarily, i.e., at medically insignificant timings while the circulatory system is normally functioning. Consequently, the measuring apparatus of the invention has considerably reduced chance of giving a discomfort to the patient due to frequent application of an occluding pressure by the cuff device, as experienced in a traditional automatic measuring apparatus wherein the measurements of the blood pressure are effected periodically irrespective of the occurrence of an abnormal condition of the subject.

BRIEF DESCRIPTION OF THE DRAWINGS

The above and other objects, features and advantages of the present invention will be better understood from reading the following description of the preferred embodiments taken in connection with the accompanying drawings in which:

FIG. 2 is a block schematic diagram showing an arrangement of a heart-beat abnormality detector used in the measuring apparatus of FIG. 1;

FIGS. 3 and 4 are flow charts representing the sequence of operation of the measuring apparatus of FIGS. 1 and 2;

FIG. 6 is a block schematic diagram showing a part of the arrangement of FIG. 5;

DETAILED DESCRIPTION OF THE PREFERRED EMBODIMENTS

Referring first to FIGS. 1–4 of the accompanying drawings, there is shown, as a non-limiting example, an automatic oscillometric blood pressure measuring apparatus embodying the invention. It is needless to say that the invention is also applicable to an automatic blood-pressure measuring apparatus of a type wherein the blood pressure measurements are made according to the presence or absence of Korotkoff sounds detected by a microphone (stethoscope), or of a type wherein the blood pressure levels are determined according to a variation in magnitude of pulsating movements of an arterial vessel wall detected by means of an ultrasonic wave.

Figure 1:
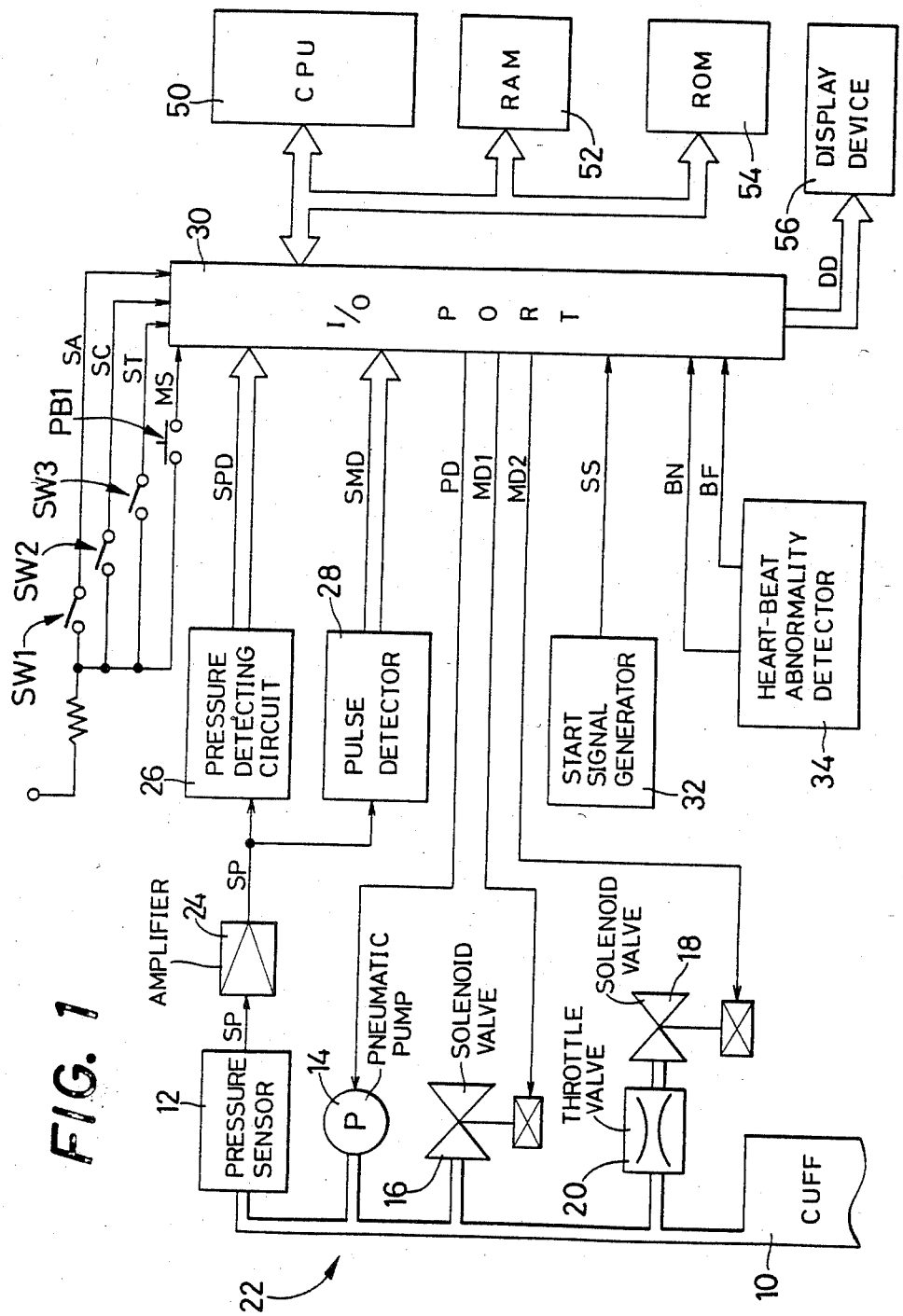
FIG. 1 is a block schematic diagram showing one embodiment of an automatic blood pressure measuring apparatus of the present invention.

There is shown in FIG. 1 a cuff 10 in the form of a tube to apply a pressure force to an arm or other body members of a human body. To this cuff 10, there are connected a pressure sensor 12 to detect a pressure in the cuff 10 and generate a PRESSURE signal SP, an electrically operated pneumatic pump 14 to build up a pressure in the cuff 10 to a given level, a RAPID-EVACUATION solenoid valve 16 to rapidly lower the pressure in the cuff 10 after completion of a blood-pressure measuring cycle, and a SLOW-EVACUATION solenoid valve 18 to slowly lower the pressure in the cuff 10. The solenoid valve 18 communicates with the cuff 10 through a flow control throttle valve 20. The cuff 10, pneumatic pump 14, solenoid valve 18, throttle vavle 20, etc. constitute an occluding device 22 for applying a pressure force to a body member of the human body and gradually releasing the pressure force.

The PRESSURE signal SP is applied to a pressure detecting circuit 26 and a pulse detector 28 via an amplifier 24. The pressure detecting circuit 26, which includes a low-pass filter and an A/D converter, filters out an static component of the PRESSURE signal SP which represents a pulse wave synchronous with blood pressure pulses of the human body. The filtered signal SP which represents a static pressure in the cuff 10 is converted into a digital code signal, i.e., into a PRESSURE signal SPD, and fed to an I/O port 30. The pulse detector 28, which includes a band-pass filter and an A/D converter, filters the PRESSURE signal SP to obtain only the oscillatory component thereof (for example, 1.0 to about 50 Hz), contrary to the pressure detecting circuit 26. The obtained oscillatory component is converted into a digital code signal, i.e., into a PULSE WAVE signal SMD and then fed to the I/O port 30.

The measuring apparatus comprises an AUTO MEASUREMENT selector switch SW1, a CYCLIC MEASUREMENT selector switch SW2, a MANUAL MEASUREMENT selector switch SW3, and a MANUAL START pushbutton PB1, which apply an AUTO MEASUREMENT signal SA, a CYCLIC MEASUREMENT signal SC, a MANUAL MEASUREMENT signal ST, and a MANUAL START signal MS, respectively, to the I/O port 30. The I/O port 30 further receives a CYCLE START signal SS which is periodically generated from a START SIGNAL generator 32 at a time interval of approx. three to five minutes, and further receives a BEAT-NUMBER ABNORMALITY signal BN and a ARRHYTHMIA signal BF, both signals being generated from a HEART-BEAT ABNORMALITY detector 34, and representing an abnormality associated with a blood circulatory system of the human body.

The HEART-BEAT ABNORMALITY detector 34, which is provided as abnormality detecting means, may be arranged as shown in FIG. 2. Described more specifically, an electrocardiographic circuit 36 is provided, which is connected to electrodes 38 attached to a cuticle of a body member of the subject to pick up a variation in electromotive force of the cuticle corresponding to beats of the heart. In response to signals from the electrodes 38, the electrocardiographic circuit 36 generates heart-beat pulse signals in synchronism with the beating action of the heart. The pulse signals are applied to a Beat-Number calculating circuit 40 and a Beat-Interval calculating circuit 42. The Beat-Number calculating circuit 40 counts a number of the heart beats per unit time based on the heart-beat pulse signals, and applies a Beat-Number signal to a BEAT-NUMBER ABNORMALITY detecting circuit 44. This detecting circuit 44 compares a counted number of the heart beats represented by the Beat-Number signal, with a preset range of heart beat number supplied from a BEAT-NUMBER setter 46. In the event that the number of actual heart beats represented by the Beat-Number signal does not fall within the preset range, the BEAT-NUMBER ABNORMALITY detecting circuit 44 presents the BEAT-NUMBER ABNORMALITY signal BN. The range of the number of heart beats to be preset on the BEAT-NUMBER setter 46 is approx. 40–180 per minute, for example. The Beat-Interval calculating circuit 42 calculates an interval between the heart beats based on the heart-beat pulse signals, and applies successive Beat-Interval signals to an ARRHYTHMIA detecting circuit 48, which compares intervals represented by these Beat-Interval signals, one interval with another, and presents the ARRHYTHMIA signal BF representing an arrhythmic heart condition when the current interval has an increase or decrease beyond a predetermined percent range, e.g., plus/minus 20%, with respect to the preceding normal interval. The ARRHYTHMIA detecting circuit 48 may be arranged so as to produce the ARRHYTHMIA signal BF when any one of the component waves P, Q, R, S and T of an electrocardiographic pulse waveform corresponding to each heart beat cycle has exhibited a deviation from normal patterns over predetermined limits.

The I/O port 30 is connected via a data bus line to control means which comprises a CPU 50, a RAM 52 and a ROM 54. According to a program stored in the ROM 54 and utilizing a temporary storage function of the RAM 52, the CPU 50 processes the various signals received by the I/O port 30, and feeds a PUMP DRIVE signal PD and SOLENOID signals MD1 and MD2 to the electric pump 14, and solenoid valves 16 and 18, respectively. The I/O port 30 is also connected to a display device 56 to which DISPLAY signals DD are applied. The display device 56 includes: a SYSTOLIC-DIASTOLIC digital indicator to indicate maximum and minimum blood pressures; a BLOOD-PRESSURE ABNORMALITY indicator to indicate an abnormal level of the measured blood pressure levels; a PULSE-NUMBER ABNORMALITY indicator to indicate an abnormal number of blood pulses per unit time; HEART-BEAT & BLOOD-PRESSURE ABNORMALITY indicator to indicate concurrent existence of abnormalities associated with the heart beats and with the blood pressure; a HEART-BEAT & BLOOD-PULSE ABNORMALITY indicator to indicate concurrent existence of abnormalities associated with the heart beats and with the blood pulse; and a DETECTOR-ERROR indicator to indicate an operating error of the HEART-BEAT ABNORMALITY detector 34. These indicators may be provided in the form of: a cathode ray tube (CRT) which provides a visible display of messages identifying the abnormalities involved; a printer which provides a print-out of such messages; or a voice synthesizer which provides a vocal indication of such messages through a speaker, as well as in the form of a light or buzzer.

Referring next to block schematic flow charts of FIGS. 3 and 4, the operation of the present measuring apparatus will be described.

At first, a step S1 is executed to check whether or not the MANUAL MEASUREMENT selector switch SW3 has been activated to select a Manual Measurement mode, i.e., to see if the MANUAL MEASUREMENT signal ST has been received by the I/O port 30. When the Manual Measurement mode has been selected, the control goes to a step S2 to check if the MANUAL START pushbutton PB1 has been activated or not, i.e., to see if the MANUAL START signal MS has been received by the I/O port 30. If not, the step S2 is repeated. If the signal MS is present, a blood-pressure measurement routine is executed in a step S3 wherein a series of blood-pressure measuring steps are successively performed to determine the blood pressure levels, and judge whether the blood pressures and blood pulses are normal or not.

Figure 4:
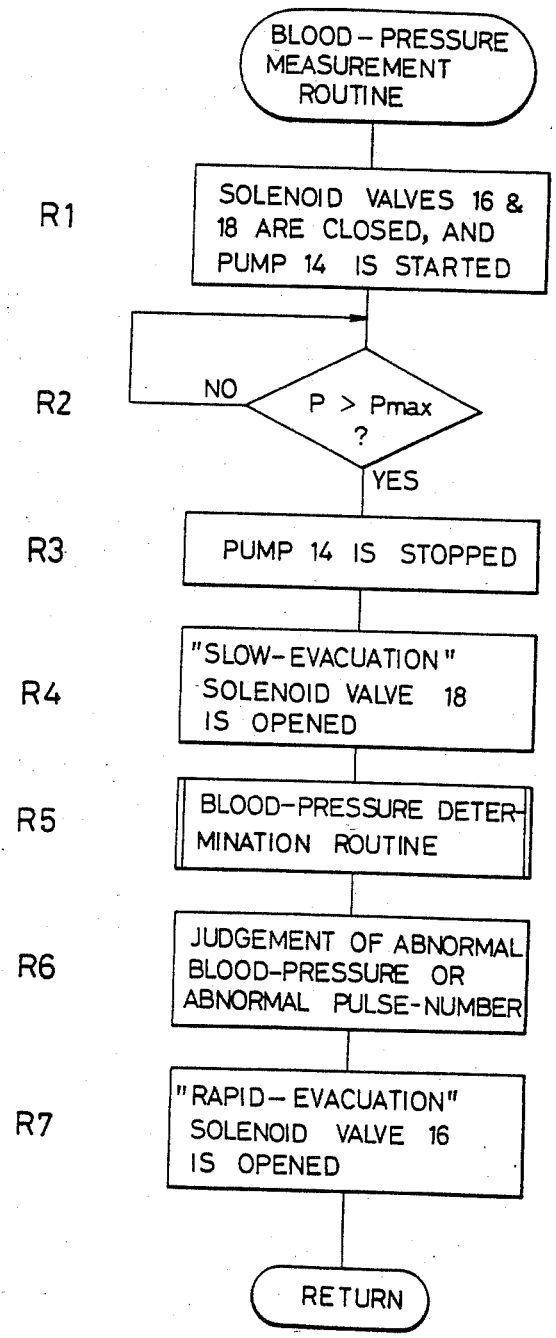
Figure 5:
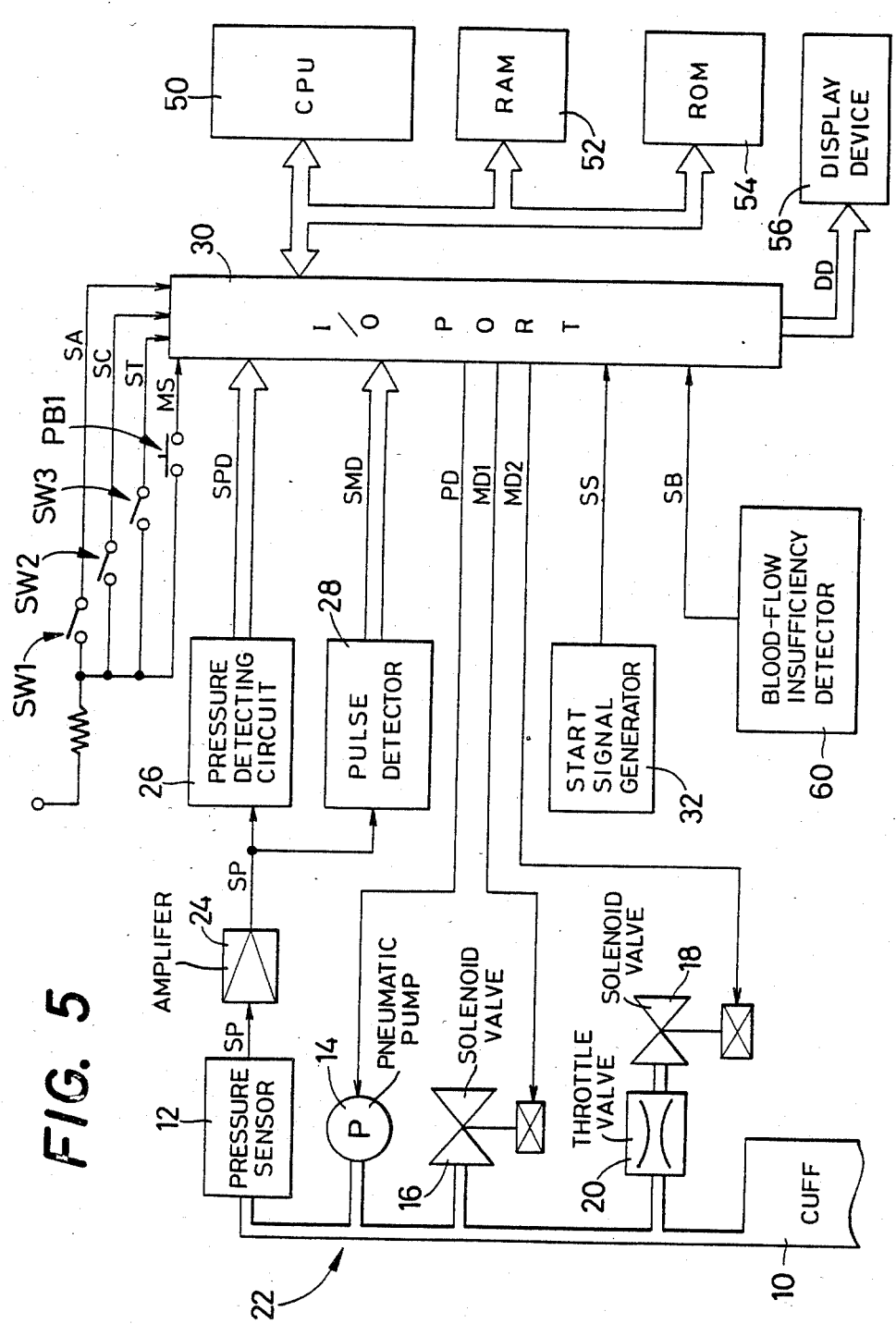
FIG. 5 is a block schematic diagram corresponding to FIG. 1, illustrating another embodiment of the measuring apparatus of the invention.

The blood-pressure measurement routine S3 is carried out as shown in FIG. 4. In a first step R1, the solenoid valves 16 and 18 are closed, and the pump 14 is operated according to the PUMP DRIVE signal PD, whereby the pressure in the cuff 10 encircling the body member of the human body is elevated and the body member is occluded with the cuff pressure. Then, the control goes to a step R2 to check if a pressure level P represented by the PRESSURE signal SPD, which indicates the actual pressure of the cuff 10, has reached a predetermined maximum pressure Pmax. If not, the step R2 is repeated. When the maximum pressure Pmax has been reached, a step R3 is executed to turn off the pump 14, thereby stopping a further rise of the cuff pressure. The maximum pressure Pmax is predetermined to be higher than a normally expected maximum or systolic blood pressure level of the subject.

The step R3 is then followed by a step R4 wherein the SLOW-EVACUATION solenoid valve 18 is opened according to the SOLENOID signal MD2, whereby the pressurized air in the cuff 10 is slowly exhausted through the throttle valve 20 and the solenoid valve 18, and consequently the pressure in the cuff 10 is gradually lowered. In the meantime, a blood-pressure determination routine is executed in a step R5 to determine the blood pressure levels, systolic and diastolic. In this blood-pressure determination routine R5, the systolic and diastolic pressure are determined from the PRESSURE signal SPD, based on a variation in amplitude of a pulse wave represented by the PULSE WAVE signal SMD which is a signal indicative of the pressure in the cuff 10. It is known that the amplitude of the above pulse wave is increased until the cuff pressure is decreased down to an average blood pressure, and is decreased as the cuff pressure is further decreased below that average point. In light of this fact, systolic and diastolic pressure levels may be detected, for example, by sensing the points of the cuff pressure in the pressuring cycle, at which amplitude increase and decrease rates of the pulse wave are maximum, respectively. Subsequently, the determined systolic and diastolic pressure levels are indicated on the display device 56. Then, a step R6 is executed to check if the measured systolic and diastolic pressures fall within a predetermined range, e.g., 70 mmHg through 150 mmHg. In the event that the measurements are outside the range, the blood pressure of the subject is judged to be abnormal. In addition, the number of the PULSE WAVE signals SMD per unit time (number of blood pulses) is continuously counted to check if the counted number is held within a predetermined range, e.g., 40–180 beats/min. If the counted value is outside this range, the blood pulses of the subject are judged to be abnormal. The control then goes to a step R7 wherein the SOLENOID signal MD1 is generated to open the RAPID-EVACUATION solenoid valve 16 for rapidly evacuating the cuff 10, whereby the body member which has been occluded, is released.

After completion of the blood-pressure measurement routine as described above, the control goes to a step S4 of FIG. 3 to check if at least one of the BEAT-NUMBER ABNORMALITY and ARRHYTHMIA signals BN and BF, is generated from the HEART-BEAT ABNORMALITY detector 34. Since this detector 34 is not usually activated when the blood pressure measurement is made in the Manual Measurement mode by operating the MANUAL START pushbutton PB1, no abnormality signals BN, BF are present. Therefore, the control goes to a step S5 to check for blood-pressure abnormality. If no blood-pressure abnormality is found, a step S6 is executed to check for pulse-number abnormality. In other words, the steps S5 and S6 are performed to check if the blood-pressure abnormality and/or the pulse-number abnormality have been detected in the step R6 of the previously stated blood pressure measurement routine. If the blood-pressure abnormality exists, a step S7 is carried out to illuminate the BLOOD-PRESSURE ABNORMALITY indicator of the display device 56. If the pulse-number abnormality exists, a step S8 is executed to illuminate the PULSE-NUMBER ABNORMALITY indicator.

In the case where the judgement in the step S1 indicates that the Manual Measurement mode has not been selected, a step S9 is executed to check if the CYCLIC MEASUREMENT signal SC is applied to the I/O port 30, i.e., to see if the CYCLIC MEASUREMENT selector switch SW2 has been activated or not. When the Cyclic Measurement mode is selected with the switch SW2, the control goes to a step S10 to see whether the I/O port 30 has received any of the CYCLE START signals SS which are periodically generated from the START SIGNAL generator 32. If the CYCLE START signal SS is not present, the step S10 is repeated. If the signal SS has been received by the I/O port 30, the control goes to the previously discussed blood-pressure measurement routine S3, wherein the systolic and diastolic blood pressures are determined, and judgements are made as to the blood-pressure and pulse-number abnormalities. Then, the control goes to the steps S4–S8, as in the Manual Measurement mode.

In the case where the judgement is made in the step S9 that the Cyclic Measurement mode is not selected, the control goes to a step S11 to check if the AUTO MEASUREMENT signal SA has been received by the I/O port 30, i.e., to see if the AUTO MEASUREMENT selector switch SW1 has been activated or not. If not, the control goes back to the step S1. If the selector switch SW1 has been activated, a step S12 is executed to check if the BEAT-NUMBER ABNORMALITY signal BN or the ARRHYTHMIA signal BF is present. If not, the step S12 is repeated. If one of these signals BN and BF is present, the blood-pressure measurement routine in the step S3 is executed as previously described, for determination of the systolic and diastolic pressures and for checking of the presence of a blood-pressure abnormality or a pulse-number abnormality.

Subsequently, the control goes to the step S4 to check for presence of the abnormality signal BN or BF. Now that the blood-pressure measurement routine S3 has been completed in the Auto Measurement mode, either one of the abnormality signals BN, BF is present. Therefore, the step S4 is followed by a step S13 to check for blood-pressure abnormality. If the blood-pressure abnormality does not exist, the step S13 is followed by a step S14 to check for blood-pulse-number abnormality. In these steps S13 and S14, therefore, the checkings are made as to whether the blood-pressure abnormality and/or the pulse-number abnormality has (have) been detected in the step R6 of the previously stated blood-pressure measurement routine. In the case where the blood-pressure abnormality exists, a step S15 is executed to activate the HEART-BEAT & BLOOD-PRESSURE ABNORMALITY indicator of the display device 56 to indicate concurrent existence of an abnormality of the blood pressure and an abnormality of the heart beat number or arrhythmia. On the other hand, in the case of the pulse-number abnormality, the step S14 is followed by a step S16 wherein the HEART-BEAT & BLOOD-PULSE ABNORMALITY indicator is activated to indicate concurrent existence of a blood-pulse abnormality and an abnormality of the heart beat number or arrhythmia. The activation of the HEART-BEAT & BLOOD-PULSE ABNORMALITY indicator shows that the abnormality of the heart beat number was not detected erroneously due to movements of the subject, that is, the subject actually suffers that abnormality, because the indicator shows that the blood pulse is also abnormal. If the judgement in the step S14 reveals that there exists no blood-pulse abnormality, a step S17 is executed to activate the DETECTOR-ERROR indicator of the display device 56, in order to indicate an operating error of the HEART-BEAT ABNORMALITY detector 34.

Stated in more detail, the HEART-BEAT ABNORMALITY detector 34 may erroneously generate the BEAT-NUMBER ABNORMALITY signal BN or the ARRHYTHMIA signal BF due to movements of the subject and consequent irregular change in electromotive force generated on the surface of the subject body. In such instance, the indication of a blood-pulse abnormality may be effectively used to make sure that such heart-beat abnormality or disorder as represented by the signal BN, BF actually takes place on the heart of the subject.

As described hitherto, the present embodiment provides the Auto Measurement mode wherein a blood pressure measuring cycle is automatically effected upon generation of each heart-beat abnormality signal BN, BF, that is, at the medically important timing when a disorder of the heart of a patient, which is an abnormality in the blood circulatory system, is found during a continuous monitoring of the patient during or after a surgical operation thereof, whereby adequate medical judgement and treatment of the patient may be made without a delay. Further, the cuff 10 applies a pressure force only at the time of trouble with the heart beats of the subject (patient), the discomfort of the patient due to occlusion of the body member by the cuff 10 is held to a minimum.

While the present invention has been described in its preferred embodiment referring to FIGS. 1–4, it is to be undersood that the invention may be otherwise embodied.

For example, only one of the BEAT-NUMBER ABNORMALITY and ARRHYTHMIA signals BN and BF generated from the HEART-BEAT ABNORMALITY detector 34 may be used as a signal indicative of abnormality of the blood circulatory system.

Further, the Beat-Number calculating circuit 40, Beat-Interval calculating circuit 42, BEAT-NUMBER ABNORMALITY detecting circuit 44 and ARRHYTHMIA detecting circuit 48, which constitute the HEART-BEAT ABNORMALITY detector 34, may be replaced by a program which is stored in the ROM 54. In this instance, the output signals from the electrocardiographic circuit 36 are applied directly to the I/O port 30.

Further, the selector switches SW1, SW2 and SW3 used in the preceding embodiment may be eliminated. In this instance, the blood-pressure measurement is accomplished only in the Auto Measurement Mode, and the steps S1, S2, S9, S10 and S11 of FIG. 3 are eliminated.

While the preceding embodiment illustrated in FIGS. 1–4 uses the HEART-BEAT ABNORMALITY detector 34 as abnormality detecting means for monitoring a blood circulatory system of the subject for normal functioning thereof, the abnormality detector 34 may be replaced by other abnormality detecting means such as BLOOD-FLOW insufficiency detector 60 employed in alternative embodiments shown in FIGS. 5–10. This detector 60 detects a blood pulse wave at a peripheral part of the subject, for example, a blood pulse wave at a finger, which corresponds to a pulsation of a blood flow through the finger, so that the detector 60 generates a BLOOD-FLOW INSUFFICIENCY signal SB to initiate a blood-pressure measuring cycle when the rate of decrease in blood flow volume through the finger has exceeded a predetermined limit.

The BLOOD-FLOW INSUFFICIENCY detector 60 is constructed as shown in FIG. 6, wherein a FINGER-TIP BLOOD-PULSE detector (transducer) 62 senses a blood pulse wave corresponding to a blood pulsation at the finger tip, and generates a FINGER-TIP BLOOD-FLOW signal S1. This signal S1 is fed to a PEAK PULSE AMPLITUDE calculating circuit 66 via an amplifier 64. The PEAK PULSE AMPLITUDE calculating circuit 66 determines a peak amplitude of the received FINGER-TIP BLOOD-FLOW signal S1, and supplies a BLOOD-FLOW INSUFFICIENCY detecting circuit 68 with a signal representing the calculated peak amplitude of the signal S1. On the other hand, the detecting circuit 68 receives from a PEAK DECLINE setter 70 a signal representing a predetermined rate of decrease in the blood flow volume. The BLOOD-FLOW INSUFFICIENCY detecting circuit 68 produces a BLOOD-FLOW INSUFFICIENCY signal SB when the rate of decrease in the calculated peak amplitude of the FINGER-TIP BLOOD-FLOW signal S1 has exceeded the predetermined rate preset on the PEAK DECLINE setter 70. The produced BLOOD-FLOW INSUFFICIENCY signal SB is applied to the I/O port 30. The rate of decrease in the peak amplitude of the signal S1 is obtained by comparing the calculated peak amplitude value (representing a current blood flow) with a preset standard peak amplitude value (representing a blood flow volume in the normal condition of the circulatory system) which is stored in the detecting circuit 68. The calculation of the decrease rate of the peak amplitude is achieved each time the FINGER-TIP BLOOD-FLOW signal S1 is applied to the detecting circuit 68. It is appreciated that the PEAK PULSE AMPLITUDE calculating circuit 66 and the PEAK DECLINE setter 70 be replaced by a circuit to integrate the signal S1 and a setter to register a rate of decrease in the integrated value of the signal S1. This replacement is possible because the volume of blood flow in the finger is represented by an area defined by the wave form of the signal S1, as well as by the peak amplitude of the signal S1.

Figure 7:
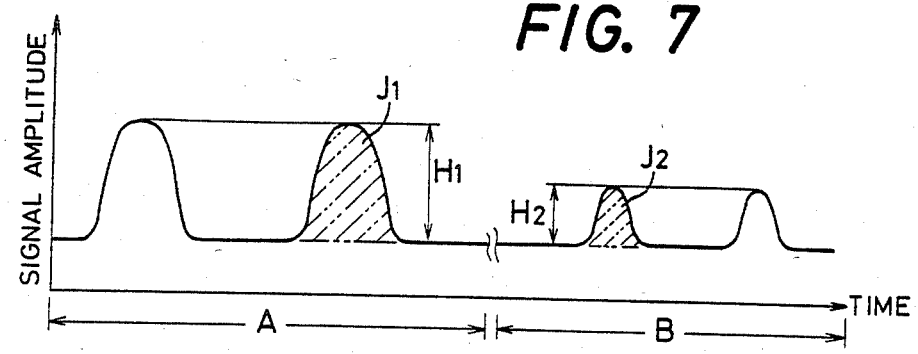
FIG. 7 is a graphical representation illustrating a wave form of a signal generated by a blood-pulse detector shown in FIG. 6.

For example, in the case where the wave form of the signal S1 in a normal condition of a patient prior to a surgical operation is as indicated at A in FIG. 7, while the signal S1 is changed as indicated at B during the surgical operation, the BLOOD-FLOW INSUFFICIENCY detecting circuit 68 calculates a decrease rate $Hr (=1-H_2/H_1)$ of the peak amplitude of the signal S1, and generates the BLOOD-FLOW INSUFFICIENCY signal SB in the event that the calculated decrease rate Hr is higher than a preset value registered on the PEAK DECLINE setter 70. In the case where a signal integrator and an integration-type setter are provided, the detecting circuit 68 calculates a decrease rate Jr $(=1-J_2/J_1)$ of an integral area of the signal S1, and generates the signal SB in the event that the calculated decrease rate Jr is higher than a preset value registered on the setter.

Figure 8:
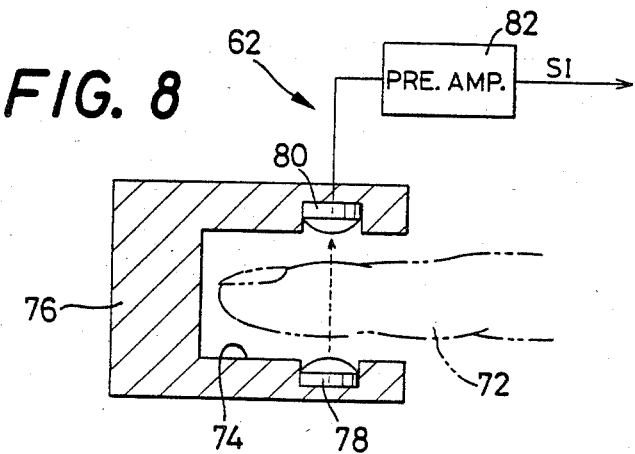
FIGS. 8 and 9 are views showing two different forms of the blood-pulse detector of FIGS. 6 and 7, respectively.
Figure 9:
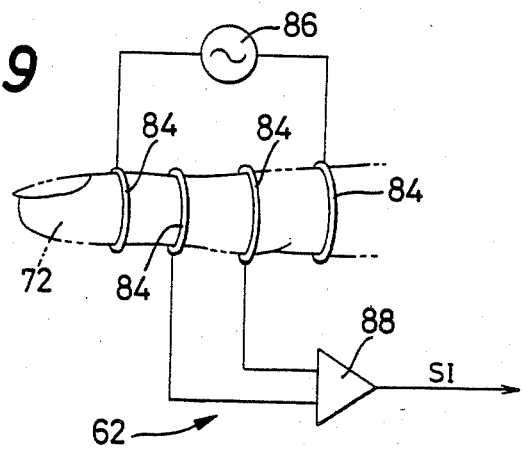

The FINGER-TIP BLOOD-PULSE detector 62 is constructed as illustrated in FIG. 8 or 9. The detector 62 of FIG. 8 comprises a photoelectric device including: a housing 76 having a bore 74 which accommodates a distal end portion 72 of the finger or finger tip 72; a light emitter 78 which emits a light beam such as infrared rays toward a surface of the finger tip; a light receiver 80 which receives the light beam transmitted through the finger tip 72; and a pre-amplifier 82 which amplifies an output signal from the light receiver 80. An amount of light transmitted (transmittance) through the finger tip 72 varies as a function of a variation in blood flow volume (number of blood cells) or in relation to a blood flow pulsation in the finger tip 72. This variation of the light transmittance is represented by a FINGER-TIP BLOOD-PULSATION signal SR (photoelectric pulse wave), and the amplitude of this signal SR corresponds to a working or functioning condition of the blood circulatory system, particularly a volume of blood flow through a limb or peripheral part of the subject.

The FINGER-TIP BLOOD-PULSE detector 62 shown in FIG. 9 comprises four annular electrodes 84 adapted to be held in contact with the distal end portion 72 of the finger and spaced from each other along the length of the finger; a power source 86 which applies an AC voltage to the two outer annular electrodes 84; and a differential amplifier 88 connected to the two inner annular electrodes 84 located inwardly of the outer electrodes 84. Since a current flow through the outer pair of annular electrodes 84 corresponds to a blood flow volume through the finger 72, an impedance value between the inner pair of the annular electrodes 84 varies as a function of the blood flow volume. Accordingly, the FINGER-TIP BLOOD-FLOW signal S1 generated from an output of the differential amplifier 88, represents a variation in the impedance value between the inner annular electrodes 84, which corresponds to the blood flow volume.

Figure 10:
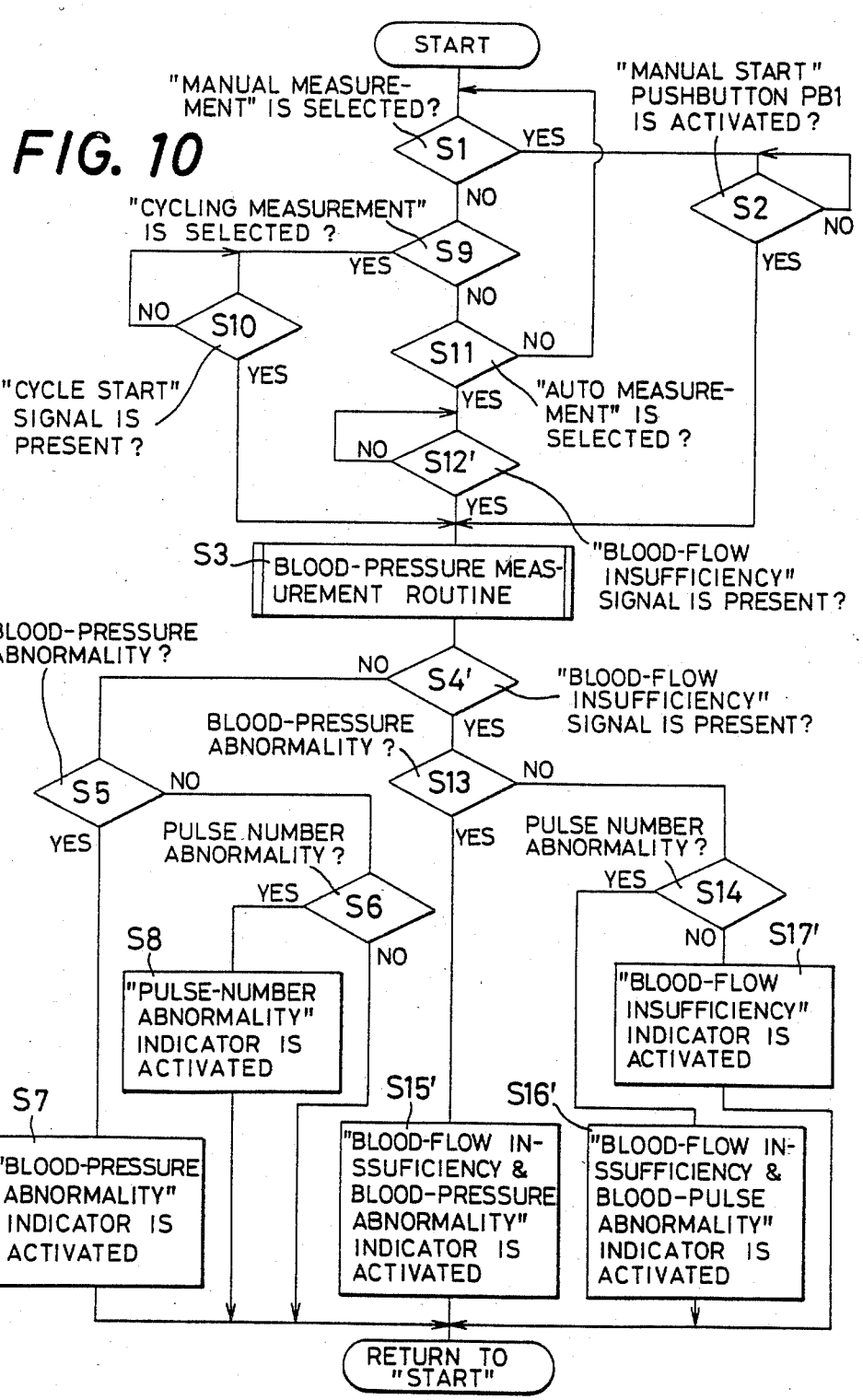
FIG. 10 is a flow chart corresponding to FIG. 3, representing the sequence of operation of the measuring apparatus of FIG. 5.

The modified embodiment of the automatic blood pressure measuring apparatus equipped with the BLOOD-FLOW INSUFFICIENCY detector 60 described above, are operated as illustrated in a flow chart of FIG. 10 which corresponds to FIG. 3 of the first embodiment. The following description of the operation of the modified embodiments refers to only operational differences thereof from the manner of operation of the first embodiment shown in FIG. 3.

While the control is placed in the Auto Measurement mode, a judgement is made in a step S12' to see if the BLOOD-FLOW INSUFFICIENCY signal SB is applied to the I/O port 30. If the judgement reveals the application of the signal SB to the port 30, the blood-pressure measurement routine S3 is executed as previously discussed. In other words, an automatic blood pressure measurement cycle is initiated when the volume of blood flow through the finger tip, which is a peripheral part of the subject, has decreased at a rate higer than a predetermined value, for example, when the volume of blood flow has decreased down to a 50%-level of a standard value. It is noted that a decrease in a blood flow volume through a peripheral part of the subject reflects, most sensitively and faithfully, a disorder of the blood circulatory system of the subject.

When the judgement in the step S13 reveals a blood-pressure abnormality, a step S15' is executed to activate an indicator for indicating concurrent existence of the blood-flow insufficiency and the blood-pressure abnormality. When the judgement in the step S13 reveals no existence of a blood-pressure abnormality and the judgement in the step S14 reveals a pulse-number abnormality, a step S16' is executed to activate an indicator for indicating concurrent existence of the blood-flow insufficiency and the pulse-number abnormality. If the case where the judgement in the step S14 reveals no existence of the pulse-number abnormality, the control goes to a step S17' to indicate only the blood-flow insufficiency.

While the embodiments described hitherto represent the preferred forms of the present invention, it is to be understood that various modifications may be made without departing from the spirit and scope of the invention.

What is claimed is:

1. An apparatus for automatically measuring blood pressure of a living subject, including an occluding device having a cuff for applying a pressure force to a body member of the subject, and blood-pressure determining means for determining the blood pressure according to a variation in a pulse wave generated at the body member in relation to a change in the pressure force applied thereto by the occluding device, said apparatus comprising:

abnormality detecting means for monitoring a blood circulatory system of said subject for normal functioning thereof, and generating an abnormality signal representing an abnormality associated with said blood circulatory system;

control means, responsive to said abnormality signal, for actuating said occluding device to apply said pressure force to said body member, and causing said blood-pressure determining means to execute a predetermined series of blood-pressure measuring steps to measure the blood pressure, thereby permitting an automatic measurement of the blood pressure of the subject when the blood circulatory system is found abnormal by said abnormality detecting means.

2. An apparatus as recited in claim 1, wherein said abnormality detecting means comprises at least one electrode adapted to be attached to a cuticle of the subject, said abnormality detecting means detecting a variation in electromotive force to detect heart beats of the subject.

3. An apparatus as recited in claim 2, wherein said abnormality detecting means comprises means for obtaining a number of said heart beats per unit time, and for generating a beat-number abnormality signal representing an abnormality associated with said number of the heat beats when said number of the heart beats does not fall within a predetermined range.

4. An apparatus as recited in claim 3, further comprising:

another abnormality detecting means for sensing blood pulses at said body member occluded by said occluding device, counting a number of said blood pulses per unit time, and judging that the counted number of the blood pulses is outside a predetermined range; and abnormality indicator means for providing a concurrent indication of the abnormality associated with the number of the heart beats, and of an abnormality associated with said counted number of the blood pulses, when both of said abnormalities associated with said numbers of the heart beats and the blood pulses are detected by said abnormality detecting means and said another abnormality detecting means, respectively.

5. An apparatus as recited in claim 3, further comprising:

another abnormality detecting means for sensing blood pulses at said body member occluded by said occluding device, counting a number of said blood pulses per unit time, and judging whether the counted number of the blood pulses is outside a predetermined range; and abnormality indicator means for indicating an operating error of said abnormality detecting means, when the abnormality associated with the number of the heart beats is detected by said abnormality detecting means and when the counted number of the blood pulses is not judged, by said another abnormality detecting means, to be outside said predetermined range.

6. An apparatus as recited in claim 2, wherein said abnormality detecting means comprises means for obtaining an interval of said heart beats, and generating an arrhythmia signal representing an arrhythmic condition of the heart when said interval does not fall within a predetermined range.

7. An apparatus as recited in claim 1, wherein said abnormality detecting means comprises a photoelectric device which senses a variation in amount of light transmitted through a finger tip of the subject and detects a blood pulse wave corresponding to a blood flow pulsation in the finger tip.

8. An apparatus as recited in claim 7, wherein said abnormality detecting means comprises means for determining a volume of a blood flow in the finger based on an amplitude of said blood pulse wave, and generating a blood-insufficiency signal representing insufficiency of the blood flow when a rate of decrease in said amount of the blood flow has exceeded a predetermined value.

9. An apparatus as recited in claim 1, wherein said abnormality detecting means has plural electrodes adapted to be held in contact with a finger of the subject and sensing a variation in impedance of the finger, said abnormality detecting means detecting a blood pulse wave corresponding to a blood flow pulsation in the finger.

10. An apparatus as recited in claim 1, further comprising:

another abnormality detecting means for judging that the blood pressure determined by said blood-pressure determining means is abnormal, when the determined blood pressure does not fall within a predetermined range; and abnormality indicator means for providing a concurrent indication of said abnormality associated with said blood circulatory system and of an abnormality of the blood pressure, when said abnormality signal is generated from said abnormality detecting means and when said determined blood pressure is judged to be abnormal by said another abnormality detecting means.

11. An apparatus as recited in claim 10, wherein said abnormality indicator means provides a concurrent indication of an abnormality associated with heart beats and of the abnormality of the blood pressure, when an abnormality associated with number of the heart beats per unit time and/or an abnormality associated with an interval of the heart beats is/are detected by said abnormality detecting means and when the abnormality of the blood pressure is detected by said another abnormality detecting means.

12. An apparatus as recited in claim 10, wherein said abnormality indicator means provides a concurrent indication of insufficiency of a blood flow in a finger of the subject, and of the abnormality of the blood pressure, when a decrease in volume of said blood flow is detected by said abnormality detecting means and when the abnormality of the blood pressure is detected by said another abnormality detecting means.

* * * * *